United States Patent [19]

Klein et al.

[11] Patent Number: 5,384,059
[45] Date of Patent: Jan. 24, 1995

[54] HEAT TRANSFER FLUID AND PROCESS FOR ITS PREPARATION

[75] Inventors: Alfons Klein, Duesseldorf; Rudolf Kron, Bornheim; Helmut Fiege, Leverkusen; Klaus-Christian Paetz, Burscheid, all of Germany

[73] Assignee: Bayer Aktiengesellschaft, Leverkusen, Germany

[21] Appl. No.: 110,343

[22] Filed: Aug. 20, 1993

Related U.S. Application Data

[63] Continuation of Ser. No. 984,788, Dec. 3, 1992, abandoned.

[30] Foreign Application Priority Data

Dec. 13, 1991 [DE] Germany ............................ 4141191

[51] Int. Cl.$^6$ .................... C07C 2/66; C07C 13/18
[52] U.S. Cl. ............................. 252/73; 252/71; 585/21; 585/26; 585/446; 585/467; 585/266
[58] Field of Search .................. 252/71, 73; 585/21, 585/26, 446, 467, 266

[56] References Cited

U.S. PATENT DOCUMENTS

| | | | |
|---|---|---|---|
| 4,681,980 | 7/1987 | Sato et al. ............................. | 585/6.3 |
| 4,840,745 | 6/1989 | Tsubouchi et al. .................. | 252/73 |
| 5,152,920 | 10/1992 | Takatsu et al. ................. | 252/299.63 |

OTHER PUBLICATIONS

Derwent Report Abstracts of the Japanese publications (J48092347; J49005949 and J49011860).
J. Org. Chem. 30 (1965), p 384 ff.

*Primary Examiner*—Asok Pal
*Attorney, Agent, or Firm*—Sprung Horn Kramer & Woods

[57] ABSTRACT

Mixtures consisting essentially of cyclohexylbiphenyls, dicyclohexylbenzenes, phenylbicyclohexyls and tercyclohexyls are outstandingly suitable as heat transfer media. The mixtures can be prepared from biphenyl and cyclohexanol in the presence of bleaching earths and subsequent hydrogenation.

10 Claims, No Drawings

HEAT TRANSFER FLUID AND PROCESS FOR ITS PREPARATION

This application is a continuation, of application Ser. No. 984,788, filed Dec. 3, 1992, now abandoned.

The invention relates to mixtures of cyclohexylbiphenyls, dicyclohexylbenzenes, phenylbicyclohexyls, tercyclohexyls and optionally higher polycyclic hydrocarbons, which mixtures are liquid at room temperature, processes for their preparation and their use as heat transfer media.

"Heat transfer media" in the sense of the invention are heat transfer agents which are used, for example, in cooling and heating circuits and in heat recovery units. Such heat transfer media are expected to have, inter alia, a high heat capacity, a high thermal loading capacity and, above all, as low as possible a viscosity, because the viscosity is one of the factors determining the required pump capacity (and thus the suitability of the heat transfer medium for use at low and high temperatures) and the flow rate (and thus the achievable heat transfer and the sizing of the heat exchange surfaces). When the heat transfer media are used for cooling purposes, the lowest possible use temperature is determined by the viscosity.

Because of their chemically inert behavior even at high temperatures, chlorinated polyphenyls were the most popular heat transfer media in the past. Since chlorinated polyphenyls have, for the known reasons, no longer been used for this purpose, there has been a switch to non-halogenated polyphenyls and their derivatives, such as, for example, partially hydrogenated terphenyls (Monsanto Company publication, Wärmeträgerflüssigkeiten (heat transfer fluids), introductory edition 1991, page 4).

Terphenyls are obtained as by-products in the preparation of biphenyl. Since the thermal biphenyl synthesis - the pyrogenic benzene dehydrogenation at 700° to 800° C. - is carried out in the presence of carbon disulphide in order substantially to prevent degradation products (carbon black!), the resulting diphenyl and the terphenyls obtained as by-products contain small amounts of sulphur compounds, which, as is known, act as catalyst poisons and therefore make the terphenyl hydrogenation more difficult. An industrially advanced preparation process should take this problem into account.

It has now been found that mixtures of partially and completely hydrogenated terphenyls of the type according to the claim have the requisite advantageous heat transfer properties.

The invention therefore relates to mixtures of
A. 4 to 30 and preferably 10 to 25% by weight of 2-cyclohexylbiphenyl,
B. 1 to 15 and preferably 3 to 9% by weight of 3-cyclohexylbiphenyl,
C. 4 to 30 and preferably 11 to 20% by weight of 4-cyclohexylbiphenyl and
D. 45 to 65% by weight of dicyclohexylbenzenes, phenylbicyclohexyls and/or tercyclohexyls and optionally higher polycyclic hydrocarbons,
the percentage data in each case relating to the sum of the components A to D.

The above mixtures according to the invention can be prepared by hydrogenation of mixtures of cyclohexylbiphenyls and terphenyls.

In the past, cyclohexylbiphenyls have been prepared by reacting biphenyl with cyclohexene or halogenocyclohexane in the presence of typical Friedel-Crafts catalysts, such as, for example, aluminium chloride (Japanese Patent 1973/92 347 of 30.11.1973; Japanese Patent 1974/5949 of 19.1.1974; Japanese Patent 1974/11 860 of 1.2.1974). However, when aluminium chloride is used, corrosion problems arise in the reactors used. It has now been found, surprisingly, that cyclohexylbiphenyls form in good yield by reaction of biphenyl with cyclohexanol in the presence of bleaching earth, which corresponds to a Friedel-Crafts alkylation of biphenyl with the cyclohexene formed from cyclohexanol.

A further subject of the invention is, therefore, a process for the preparation of cyclohexylbiphenyls from biphenyl and cyclohexanol in the presence of 0.3 to 5 and preferably 0.8 to 2% by weight of bleaching earth, based on biphenyl employed.

In this reaction the molar ratio of the starting materials biphenyl and cyclohexanol can vary within wide limits; it is generally 1 to 5 and preferably 2 to 3.

The reaction temperature is generally 140° to 220° C., preferably 160° to 190° C. "Bleaching earths" are understood to be finely divided materials which essentially are derived from aluminium oxides and/or silicon oxides - preferably those having a strip or plate structure. Preferred bleaching earths comprise predominantly aluminosilicates such as the montmorillonite group, which includes bentonites, nontronites, baydellites and hectorites, but also kaolins, as well as essentially quartz-like products, such as kieselguhr and related deposits. Bleaching earths of this type can be used without pretreatment; preferably, however, they are subjected to a treatment with acid, in particular with an inorganic acid such as sulphuric acid, phosphoric acid, hydrochloric acid, perchloric acid or hydrofluoric acid. "Activated" bleaching earths of this type are described, for example, in Ullmanns Encyclopädie der technischen Chemie (Ullmann's Encyclopaedia of Industrial Chemistry), 3rd edition, volume 4, page 541 et seq. (1953), volume 8, pages 801 to 804 (1957) and volume 9, page 271 et seq. (1957), Urban & Schwarzenberg, Munich-Berlin.

According to the invention, the procedure can, for example, be carried out in such a way that biphenyl and bleaching earth are initially introduced and cyclohexanol is supplied at elevated temperature. The resulting water of reaction can be distilled off continuously with the cyclohexene, which is initially formed, and separated off using a water separator. The recycled cyclohexene then serves for alkylation of the biphenyl. For working up, the reaction mixture can be filtered hot, with suction, to remove the catalyst. Excess biphenyl will then be distilled off. The distillation residue, which essentially consists of cyclohexylbiphenyls, can be processed without further purification steps or purified by distillation.

It is self-evident that when cyclohexylbiphenyls are prepared higher polycyclic hydrocarbons having more than 3 rings per molecule (for example dicyclohexylbiphenyls) can also form as by-products (the individual rings of these polycycles having no common ring atom and no common ring bond). The amount of these higher polycyclic by-products will not exceed 20% by weight, preferably 15% by weight, of the biphenyl-free reaction product of the cyclohexylbiphenyl preparation. Insofar as the individual isomers (for example "2-cyclohexylbiphenyl") are not mentioned, the expression "cyclohexylbiphenyl" in the sense of the invention signifies the reaction product from the cyclohexylbiphenyl preparation including the higher polycyclic hydrocarbons formed as by-products.

Furthermore, it has been found, surprisingly, that the terphenyl problem described further above can also be satisfactorily resolved using bleaching earth: if bleaching earth is allowed to act on the mixture of terphenyls and cyclohexylbiphenyls intended for hydrogenation and is then separated off, products are obtained which (compared with untreated mixtures) can be hydrogenated considerably more rapidly. Because of the high melting point of the mixture, the separation of bleaching earth from batches on an industrial scale presents difficulties. The reaction proceeds considerably more simply if the mixture is diluted with additional biphenyl. A mixture of this type can be prepared in connection with the synthesis of cyclohexylbiphenyls:

Following the reaction of excess biphenyl with cyclohexanol in the presence of bleaching earth, crude terphenyl is added to the reaction mixture and the mixture is stirred for 0.5 to 4 hours at 130° to 160° C. It is then possible to filter off the bleaching earth from the hot mixture, with suction, to distil off the excess biphenyl and to feed the residue to the hydrogenation. This residue can be hydrogenated in approximately the same time as a mixture of cyclohexylbiphenyls and sulphur-free terphenyls.

A further subject of the invention is, therefore, a process for the preparation of the instant heat transfer fluids by partial hydrogenation of a mixture of terphenyls and cyclohexylbiphenyls, characterised in that the mixture used for the hydrogenation, or its components, is/are treated with bleaching earth.

In accordance with the above statements with regard to the higher polycyclic hydrocarbons possibly contained in the cyclohexylbiphenyls as by-products, the mixtures of terphenyls and cyclohexylbiphenyls intended for hydrogenation can also contain these higher polycyclic hydrocarbons; the hydrogenation products can also contain these higher polycyclic hydrocarbons or their hydrogenation products.

The hydrogenation is as a rule carried out under moderately elevated pressure and at elevated temperature in the presence of 1 to 10, preferably 3 to 6%, by weight of a hydrogenation catalyst, for example a nickel catalyst. In general, finely divided metallic nickel on a support or in the form of Raney nickel is used. The hydrogenation can be discontinued when the proportion D of the mixtures according to the claim is in the range of 45 to 65% by weight, based on the sum of the components A to D.

As is known, aromatic compounds can be hydrogenated only under forced conditions. For aromatic ring hydrogenations, pressures of at least 100 bar and temperatures of above 250° C. are generally employed (J. Org. Chem., Vol. 30 (1965), p. 384–388; Ullmanns Encyclopädie der technischen Chemie (Ullmann's Encyclopaedia of Industrial Chemistry), 4th edition, volume 9, page 683, Urban & Schwarzenberg, Munich-Berlin 1975). It was therefore completely surprising that the hydrogenation of a mixture of terphenyls and cyclohexylbiphenyls can take place under relatively mild conditions. Instead of expensive high-pressure autoclaves it is thus now possible to use normal reactors.

A further subject of the invention is, therefore, a process for the preparation of mixtures according to claim 1 by partial hydrogenation of a mixture of terphenyls and cyclohexylbiphenyls in the presence of a hydrogenation catalyst, characterised in that the hydrogenation is carried out at temperatures of 120° to 190° C., preferably of 160° to 180° C., and under pressures of 2 to 25, preferably 8 to 15, bar.

The statements made further above apply in respect of the nature of the suitable catalyst and the end of the hydrogenation.

A further aim of the invention was the provision of an overall concept for the preparation of a modern heat transfer medium using biphenyl and terphenyl as starting materials on as economical a basis as possible. The implementation of the processes described represents such a concept using biphenyl and terphenyl as starting materials, which concept leads to the instant heat transfer fluids.

A further subject of the invention is, therefore, a process for the preparation of instant heat transfer fluids, according to which process biphenyl and cyclohexanol are heated in a molar ratio of (1 to 5):1 in the presence of 0.3 to 5% by weight, based on biphenyl employed, of bleaching earth to a temperature of 140° to 220° C. in which process the water liberated is removed as an azeotrope together with a portion of the cyclohexene formed and the cyclohexene is recycled, terphenyl, in 0.5 to 1.2 times the amount of cyclohexylbiphenyls present in the reaction mixture, and biphenyl, in an amount such that the proportion of biphenyl in the crude mixture (after the addition of terphenyl) is at least 30% by weight, are added to the resulting reaction mixture and the resulting mixture is stirred at a temperature of 130° to 160° C. for 0.5 to 4 hours, the bleaching earth and biphenyl are separated off, the residue is hydrogenated in the presence of a hydrogenation catalyst at a temperature of 120° to 190° C. and under a pressure of 2 to 25 bar until the proportion D in the mixtures according to the claim is in the range of 45 to 65% by weight, based on the components A to D, the hydrogenation catalyst is separated off and the residual reaction mixture is distilled.

The mixtures according to the invention have a kinematic viscosity of 80 to 90 mm$^2$/sec at 20° C. Because of the high boiling points of the individual components, the mixtures according to the invention are outstandingly suitable as heat transfer media in systems under normal pressure.

A further subject of the invention is the use of the mixtures according to the invention as heat transfer media.

The percentage data in the examples which follow in each case relate to the weight; parts are parts by weight.

EXAMPLES

Example 1

A) Preparation of cyclohexylbiphenyls 981.6 g of biphenyl and 12.5 g of bleaching earth (®Tonsil KSFO from Südchemie, bleaching earth activated with sulphuric acid) are initially introduced into a 2 l three-necked flask provided with a water separator. 214 g of cyclohexanol are allowed to run in dropwise at 160° C. in the course of 5 hours. The resulting water of reaction (about 36 ml) passes over as an azeotrope with a little cyclohexene formed in the meantime and is removed from the cycle. The mixture is stirred for a further 5 hours at 180° C. and is then filtered with suction at 100° to 120° C. In the subsequent distillation through a 30 cm column, excess biphenyl is distilled off. 677 g of recyclable biphenyl are obtained.

The distillation is then continued. The resulting distillate weighs 425 g.

B) Hydrogenation 87 g of cyclohexylbiphenyl, 87 g of terphenyl and 3 g of Raney nickel are hydrogenated in an autoclave at 160° C. and under a constant pressure of 10 bar hydrogen. Following an uptake of 70 bar hydrogen, the hydrogenation is ended. The reaction mixture is filtered hot, with suction, to remove the catalyst and 170 g of the composition according to the invention, which has a kinematic viscosity of 81 mm²/sec at 20° C., are obtained. This composition contains:

| | |
|---|---|
| 2-cyclohexylbiphenyl: | 13.1% |
| 3-cyclohexylbiphenyl: | 6.2% |
| 4-cyclohexylbiphenyl: | 19.1% |
| mixture of dicyclohexylbenzenes, phenylbicyclohexyls, tercyclohexyls and higher polycyclic hydrocarbons: | 61.6% |

Example 2

A) Preparation of cyclohexylbiphenyls 653 g of biphenyl and 12.5 g of Tonsil KSFO are initially introduced into a three-necked flask provided with a water separator. 214 g of cyclohexanol, which contains 1% of water to lower the solidification point, are allowed to run in dropwise at 160° C. in the course of 5 hours. The resulting water of reaction (about 39 ml) passes over as an azeotrope with a little cyclohexene formed in the meantime and is removed from the cycle. The reaction mixture is stirred for a further 5 hours at 180° C. The resulting crude product (including bleaching earth) weighs 841 g.

410 g of crude, sulphur-containing terphenyl are added to this crude product at 140° C. and the resulting mixture is stirred at this temperature for half an hour. Subsequent filtering with suction is carried out at 130° to 140° C.

Excess biphenyl is distilled off in a distillation through a 20 cm column. 385 g of recyclable biphenyl are obtained up to a transfer of b.p.$_{20mmHg}$/165° C. The distillation residue weighs 819 g and is fed to the hydrogenation.

B) Hydrogenation 174 g of the mixture from batch A and 8 g of moist Raney nickel are placed in a 0.7 l autoclave. The hydrogenation pressure is kept constant at 10 bar from a 0.7 l storage vessel containing 100 bar of hydrogen by means of a reducing valve. The temperature is 180° C. The hydrogenation is ended when 75 bar of hydrogen have been taken from the storage vessel. A period of 150 minutes is required for this. After filtering off the nickel, with suction, the final distillation of the filtrate is carried out over a distillation bridge:

| | |
|---|---|
| b.p.$_{0.5mmHg}$ 115 - about 220° C.: | 164 g |
| residue: | 9.5 g |

The resulting distillate is of low viscosity, clear and soluble in toluene; it has a kinematic viscosity of 89 mm²/sec at 20° C. It contains:

| | |
|---|---|
| 2-cyclohexylbiphenyl: | 16.9% |
| 3-cyclohexylbiphenyl: | 5.6% |
| 4-cyclohexylbiphenyl: | 14.5% |
| mixture of dicyclohexylbenzenes, phenylbicyclohexyls, tercyclohexyls and higher polycyclic hydrocarbons: | 63.0% |

Claims:

1. A heat transfer fluid comprising
   A. 4 to 30% by weight of 2-cyclohexylbiphenyl,
   B. 1 to 15% by weight of 3-cyclohexylbiphenyl,
   C. 4 to 30% by weight of 4-cyclohexylbiphenyl and
   D. 45 to 65% by weight of dicyclohexylbenzenes, phenylbicyclohexyls and/or tercyclohexyls and optionally higher polycyclic hydrocarbons,
   the percentage data in each case relating to the sum of the components A to D.

2. A heat transfer liquid according to claim 1, comprising
   10 to 25% by weight of A,
   3 to 9% by weight of B,
   11 to 20% by weight of C and
   45 to 65% by weight of D.

3. A heat transfer fluid which comprises
   A. 4 to 30% by weight of 2-cyclohexylbiphenyl,
   B. 1 to 15% by weight of 3-cyclohexylbiphenyl,
   C. 4 to 30% by weight of 4-cyclohexylbiphenyl and
   D. 45 to 65% by weight of dicyclohexylbenzenes, phenylbicyclohexyls and/or tercyclohexyls and optionally higher polycyclic hydrocarbons,
   which is produced by partial hydrogenation of a mixture of terphenyls and cyclohexylbiphenyls in the presence of a hydrogenation catalyst, the hydrogenation being carried out at a temperature of 120° to 190° C., and under a pressure of 2 to 25 bar.

4. A heat transfer fluid of claim 3, wherein the hydrogenation is carried out at a temperature of 160° to 180° C. and under a pressure of 8 to 15 bar.

5. A heat transfer fluid according to claim 3, wherein the biphenyl and the cyclohexanol are heated in a molar ratio of (1 to 5):1 in the presence of 0.3 to 5% by weight, based on biphenyl employed, of bleaching earth to a temperature of 140° to 220° C., in which process the water liberated is removed as an azeotrope together with a portion of the cyclohexene formed and the cyclohexene is recycled; terphenyl, in 0.5 to 1.2 times the amount of cyclohexylbiphenyls present in the reaction mixture, and biphenyl, in an amount such that the proportion of biphenyl in the crude mixture (after the addition of terphenyl) is at least 30% by weight, are added to the resulting reaction mixture; the resulting mixture is stirred at a temperature of 130° to 160° C. for 0.5 to 4 hours; the bleaching earth and biphenyl are separated off, the residue is hydrogenated in the presence of a hydrogenation catalyst at a temperature of 120° to 190° C. and under a pressure of 2 to 25 bar until the proportion D in the mixture is in the range of 45 to 65% by weight based on the components A to D; the hydrogenation catalyst is separated off and the residual reaction mixture is distilled.

6. A process for the preparation of a cyclohexylbiphenyl, comprising reacting biphenyl and cyclohexanol in a molar ratio of (1 to 5):1 at a temperature of 140° to 220° C. in the presence of 0.3 to 5% by weight of bleaching earth, said % by weight being based on the amount of biphenyl employed.

7. A process according to claim 6, wherein 0.8 to 2% by weight of bleaching earth are employed, said % by weight being based on the amount to biphenyl employed.

8. A process for the preparation of a heat transfer fluid comprising the following ingredients:
   A. 4 to 30% by weight of 2-cyclohexylphenyl;
   B. 1 to 15% by weight of 3-cyclohexylbiphenyl;
   C. 4 to 30% by weight of 4-cyclohexylbiphenyl; and
   D. 45 to 65% by weight of dicyclohexylbenzenes, phenylbicyclohexyls and/or tercyclohexyls and optionally higher polycyclic hydrocarbons;
said process comprising treating a mixture of terphenyls and cyclohexylbiphenyls or components of the mixture with bleaching earth followed by partially hydrogentating the treated mixture with a hydrogenation catalyst at temperatures of 120° to 190° C. and under pressures of 2 to 25 bar.

9. A process according to claim 8, wherein the partial hydrogenation is carried out at temperatures of 160° to 180° C. and under pressures of 8 to 15 bar.

10. A process for the preparation of a heat transfer fluid comprising the following ingredients:
   A. 4 to 30% by weight of 2-cyclohexylbiphenyl;
   B. 1 to 15% by weight of 3-cyclohexylbiphenyl; 4 to 30% by weight of 4-cyclohexylbiphenyl; and
   D. 45 to 65% by weight of dicyclohexylbenzenes, phenylbicyclohexyls and/or tercyclohexyls and optionally higher polycyclic hydrocarbons;
said process comprising:

(a) heating to 140° to 220° C. a mixture of biphenyl and cyclohexanol in a molar ratio of (1 to 5):1 in the presence of 0.3 to 5% by weight of bleaching earth, said by weight of bleaching earth being based on the amount to biphenyl employed to yield a reaction mixture;

(b) removing from said reaction mixture water liberated as a result to said heating, said water being removed as an azeotrope together with a portion to the cyclohexene formed, and recycling said cyclohexene to said reaction mixture;

(c) adding to the reaction mixture terphenyl, in an amount to 0.5 to 1.2 times the amount of cyclohexylbiphenyls in the reaction mixture, and biphenyl, in an amount such that the proportion of biphenyl in the reaction mixture latter the addition of terphenyl is at least 30% by weight, and stirring the resulting reaction mixture at a temperature of 130° to 160° C. for 0.5 to 4 hours;

(d) separating off the bleaching earth and biphenyl; and (e) hydrogenating the resulting residue in the presence of a hydrogenation catalyst at a temperature of 120° to 190° C. and under a pressure of 2 to 25 bar until the proportion of ingredient D is in the range of 45 to 65% by weight, said % by weight being based on components A to D, then separating off the hydrogenation catalyst and distilling the residual reaction mixture.

* * * * *

UNITED STATES PATENT AND TRADEMARK OFFICE
CERTIFICATE OF CORRECTION

PATENT NO. : 5,384,059
DATED : January 24, 1995
INVENTOR(S) : Klein, et al.

It is certified that error appears in the above-indentified patent and that said Letters Patent is hereby corrected as shown below:

| | |
|---|---|
| Col. 7, line 25 | Before " 4 to " insert -- C. -- |
| Col. 8, line 4 | After " said " insert -- % -- |
| Col. 8, line 8 | Delete " to " and substitute -- of -- |
| Col. 8, line 9 | Delete " to " and substitute -- of -- |
| Col. 8, line 16 | Delete " latter " and substitute -- after -- |

Signed and Sealed this

Fifteenth Day of July, 1997

Attest:

BRUCE LEHMAN

*Attesting Officer*  *Commissioner of Patents and Trademarks*